(12) United States Patent
Mozdzierz et al.

(10) Patent No.: US 12,714,427 B2
(45) Date of Patent: Aug. 25, 2026

(54) SYSTEM AND METHOD FOR REAL-TIME TISSUE PERFUSION ASSESSMENT DURING CLAMPING

(71) Applicant: Covidien LP, Mansfield, MA (US)

(72) Inventors: Patrick D. Mozdzierz, Glastonbury, CT (US); David M. Scampoli, South Glastonbury, CT (US); Thomas C. Niemiec, Berlin, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 19/267,218

(22) Filed: Jul. 11, 2025

(65) Prior Publication Data

US 2026/0026813 A1 Jan. 29, 2026

Related U.S. Application Data

(60) Provisional application No. 63/674,990, filed on Jul. 24, 2024.

(51) Int. Cl.

| | |
|---|---|
| ***A61B 17/072*** | (2006.01) |
| ***A61B 5/00*** | (2006.01) |
| ***A61B 5/026*** | (2006.01) |
| ***A61B 5/1455*** | (2006.01) |
| ***A61B 17/00*** | (2006.01) |
| ***A61B 17/115*** | (2006.01) |

(52) U.S. Cl.

CPC ...... *A61B 17/07207* (2013.01); *A61B 5/0261* (2013.01); *A61B 5/14551* (2013.01); *A61B 5/6887* (2013.01); *A61B 5/7271* (2013.01); *A61B 5/746* (2013.01); *A61B 17/115* (2013.01); *A61B 2017/00022* (2013.01); *A61B 2017/00119* (2013.01); *A61B 2017/00398* (2013.01); *A61B 2017/07257* (2013.01); *A61B 2017/07271* (2013.01); *A61B 2560/0462* (2013.01)

(58) Field of Classification Search

None

See application file for complete search history.

(56) References Cited

U.S. PATENT DOCUMENTS

| | | | | |
|---|---|---|---|---|
| 10,624,616 B2 * | 4/2020 | Mukherjee | ........... | A61B 5/0084 |
| 2009/0234248 A1 * | 9/2009 | Zand | .................... | A61B 17/115 600/587 |

(Continued)

FOREIGN PATENT DOCUMENTS

| | | | | |
|---|---|---|---|---|
| CN | 113017738 A * | 6/2021 | ......... | A61B 5/14551 |
| WO | 2024003699 A1 | 1/2024 | | |

*Primary Examiner* — Tanzim Imam

(57) ABSTRACT

A surgical stapler system for real-time tissue perfusion assessment during clamping includes a powered surgical stapler with a handle assembly, adapter assembly, and an end effector comprising a reload assembly with staples and an anvil assembly. Integrated into the system is a near-infrared spectroscopy (NIRS) system featuring light sources and photodetectors. The method involves clamping tissue between the reload and anvil assemblies, transmitting near-infrared light through the clamped tissue, and detecting backscattered light to determine tissue perfusion levels. The perfusion data is processed and displayed in real-time, allowing adjustments to the clamping force to ensure adequate perfusion before stapling. The system enhances surgical outcomes by providing real-time feedback on tissue viability during critical phases of the stapling procedure.

20 Claims, 12 Drawing Sheets

(56) References Cited

U.S. PATENT DOCUMENTS

| | | | | |
|---|---|---|---|---|
| 2011/0282170 | A1* | 11/2011 | Bannerjee | A61B 5/6833<br>600/341 |
| 2014/0288386 | A1* | 9/2014 | Zand | A61B 5/1459<br>600/301 |
| 2014/0309666 | A1* | 10/2014 | Shelton, IV | A61B 17/072<br>606/139 |
| 2019/0038136 | A1* | 2/2019 | Gunn | A61B 5/489 |
| 2022/0257125 | A1* | 8/2022 | Zand | A61B 5/7405 |

* cited by examiner

SYSTEM AND METHOD FOR REAL-TIME TISSUE PERFUSION ASSESSMENT DURING CLAMPING

CROSS-REFERENCE TO RELATED APPLICATIONS

This application claims the benefit of U.S. Provisional Patent Application Ser. No. 63/674,990, filed Jul. 24, 2024, the entire content of which is incorporated herein by reference.

BACKGROUND

1. Technical Field

The present disclosure relates to surgical devices. More specifically, the present disclosure relates to electromechanical surgical systems for performing stapling surgical procedures.

2. Background of Related Art

Surgical fastener devices for applying fasteners or staples to tissue are well known. These fastener devices include surgical staplers, which may be manual or motor-powered. There are multiple types of powered surgical staplers, such as linear or circular staplers, which are specifically designed to perform certain types of surgical procedures, including endoscopic procedures that provide a real-time video of a surgical site through a laparoscopic or endoscopic camera.

Linear staplers are used in a variety of surgical procedures, such as resection and transection of organs and other tissues. Circular staplers are used to reattach rectum portions that were previously transected, or similar procedures. Linear and circular staplers may be manually actuated or may be powered and may include a pistol or linear grip-styled structure having an elongated shaft extending therefrom and a staple cartridge supported on the distal end of the elongated shaft.

With respect to circular staplers, a physician may insert an anvil assembly of the circular stapling instrument through an incision and toward the transected rectum portions. The physician may also insert the remainder of the circular stapling instrument (including the cartridge assembly) into a rectum of a patient and maneuver the instrument up the colonic tract of the patient toward the transected rectum portions. The anvil and cartridge assemblies are approximated toward one another, and staples are ejected from the cartridge assembly toward the anvil assembly to form the staples in tissue to affect an end-to-end anastomosis, and an annular knife is advanced to core a portion of the clamped tissue portions. After the end-to-end anastomosis has been affected, the circular stapling apparatus is removed from the surgical site.

Following a stapling procedure, linear or circular, maintaining adequate blood flow in the staple line region supports tissue recovery. Currently, there is a need for instruments that can evaluate vascularization among the staples as a measure of adequate blood flow in the staple line region.

SUMMARY

The present disclosure provides a powered stapler (e.g., circular or linear) that is configured to form a staple line, e.g., a linear staple line or an anastomosis by connecting two portions of a structure (e.g., intestine, colon, etc.). The powered stapler includes a handle assembly having a power source and one or more motors coupled to the power source. The stapler also includes an adapter assembly having multiple transmission assemblies, e.g., drive shafts, which transmit actuation from the powered handle. The powered handle assembly and the adapter assembly may be reusable.

The powered surgical staplers operate in four phases, namely, clamping, stapling, cutting, and unclamping. For the linear stapler, clamping, stapling, and cutting occur while a drive shaft is advanced, and unclamping occurs during reversal of the drive shaft.

For circular staplers, clamping is accomplished by moving the anvil in a proximal direction to compress tissue between the anvil and a reload assembly, which includes a plurality of staples. The anvil and the reload assembly may be disposable. During stapling, the staples are ejected from the reload assembly into the clamped tissue and are deformed against the anvil. Cutting includes moving an annular knife through the compressed and stapled tissue until the knife contacts the anvil. During unclamping, the anvil assembly is moved distally away from the cut tissue and the reload assembly.

The powered stapler includes a real-time near infrared spectroscopy (NIRS) system which provides blood flow measurement within the reload assembly to allow estimation of tissue perfusion during the stapling procedure. The NIRS system, which may also include diffused correlation spectroscopy, is an optical method to assess blood flow in tissues using near-infrared light (NIR) (e.g., NIR light having a wavelength from about 700 nm to about 900 nm). Depending on the source-detector distance, light travels through different depths of tissues, and analysis of the collected backscattered light indicates blood flow levels within the tissue. One or more light sources and detector(s) may be disposed within the circular stapler to allow tissue perfusion or oximetry assessment around the staple line during or after the procedure.

The NIRS system according to the present disclosure may be incorporated into any surgical stapler, i.e., circular, linear, etc., with the light sources and detectors being interspersed along a staple line. In particular, the light source, which may be a laser, and a detector may be incorporated within the linear and/or circular stapler designs to create a reflective photoplethysmography to measure staple line profusion.

In embodiments, the NIRS system may include a ring-shaped or linear flex circuit disposed adjacent, e.g., behind, staple guides of the reload assembly. The flex circuit may be placed along the outer row of the staple line, adjacent any staple row, e.g., inner row, middle row, etc. One or more light sources (e.g., LEDs, IR LEDs, combined IR and red LEDs, or other light sources) shine light through openings in the staple guide, and any light reflected back through the tissue toward photodetectors (e.g., photodiodes) interspersed in between the light sources. The light sources and photodetectors may be individually addressable, allowing for determination of profusion at a specific photodiode location.

The flex circuit may be routed to a wiring harness, which connects the NIRS system to the adapter and the handle assembly. An analog-to-digital (A/D) conversion may take place at a distal end of the adapter or on the flex circuit itself since an analog signal transmitted along the wiring harness would be susceptible to electromagnetic interference. In embodiments, transmission may be done wirelessly. In further embodiments, the signals from the photodetectors may be received at a processing unit disposed within the powered handle, connected to the detector by optical fibers through the adapter. In embodiments, the light sources and photodetectors may be coupled to an optical connector such that light is transmitted through optical fibers disposed through each component of a powered surgical stapler (e.g., end effector, adapter, handle).

According to one embodiment of the present disclosure, a surgical stapler is disclosed. The surgical stapler includes a motor, a staple cartridge having a plurality of staples, and an anvil movable by the motor relative to the staple cartridge and configured to compress tissue therebetween. The stapler also includes a spectroscopy assembly having a plurality of light sources and a plurality of photodetectors interspersed among the plurality of light sources and a controller coupled to the spectroscopy assembly. The controller is configured to activate the motor during a first phase of clamping to move the anvil to clamp tissue between the anvil and the staple cartridge and measure an oxygen saturation value in the tissue using the spectroscopy assembly. The controller is also configured to compare the oxygen saturation value to a first oxygen saturation range and output a first message indicating inadequate blood flow if the oxygen saturation value is outside the first oxygen saturation range. The controller is further configured to activate the motor during a second phase of the clamping to move the anvil to further clamp tissue between the anvil and the staple cartridge if the oxygen saturation value is within the first oxygen saturation range.

According to another embodiment of the present disclosure, a surgical stapler is disclosed. The surgical stapler includes an annular reload having a staple cartridge having a plurality of staples. The stapler may include an anvil movable relative to the annular reload and configured to compress tissue therebetween and a knife disposed within the annular reload configured to cut the tissue. The stapler also includes a spectroscopy assembly disposed within the staple cartridge and may include a plurality of light sources and a plurality of photodetectors interspersed among the plurality of light sources. The stapler further includes a handle assembly having a motor configured to move the anvil and a controller coupled to the spectroscopy assembly. The controller is configured to activate the motor during a first phase of clamping to move the anvil to clamp tissue between the anvil and the staple cartridge, activate the plurality of light sources to irradiate the tissue contacting the staple cartridge with a light, receive signals from the plurality of photodetectors based on reflected light detected by the plurality of photodetectors, and measure an oxygen saturation value in the tissue based on the signals. The controller is further configured to compare the oxygen saturation value to a first oxygen saturation range and output a first message indicating inadequate blood flow if the oxygen saturation value is outside the first oxygen saturation range. The controller is additionally configured to activate the motor during a second phase of the clamping to move the anvil to further clamp tissue between the anvil and the staple cartridge if the oxygen saturation value is within the first oxygen saturation range.

Implementations of the above embodiments may include one or more of the following features. According to one aspect of the above embodiment, the surgical stapler may also include a display configured to show a graphical user interface, where the controller is further configured to output the oxygen saturation and the first message on the graphical user interface. During the first phase, the motor may be moved at a first speed. During the second phase, the motor may be moved at a second speed, slower than the first speed. During the second phase, the controller may be further configured to measure the oxygen saturation value in the tissue and compare the oxygen saturation value to a second oxygen saturation range. During the second phase, the controller may be further configured to measure a gap distance between the anvil and the staple cartridge and compare the measured gap distance to a gap distance range. During the second phase, the controller may be also configured to enable stapling if the oxygen saturation value is within the second oxygen saturation range and the measured gap distance is within the gap distance range. During the second phase, the controller may be additionally configured to output a second message indicating inadequate blood flow if the oxygen saturation value is outside the second oxygen saturation range.

According to a further embodiment of the present disclosure, a method for real-time tissue perfusion assessment during a clamping procedure using a powered surgical stapler is disclosed. The stapler includes a motor, a staple cartridge having a plurality of staples, and an anvil movable by the motor relative to the staple cartridge. The method includes activating the motor during a first phase of clamping to move the anvil to clamp tissue between the anvil and the staple cartridge. The method also includes measuring an oxygen saturation value in the tissue using a spectroscopy assembly disposed in the staple cartridge and comparing the oxygen saturation value to a first oxygen saturation range. The method further includes outputting a first message indicating inadequate blood flow if the oxygen saturation value is outside the first oxygen saturation range and activating the motor during a second phase to move the anvil to further clamp tissue between the anvil and the staple cartridge if the oxygen saturation value is within the first oxygen saturation range.

Implementations of the above embodiment may include one or more of the following features. According to one aspect of the above embodiment, the method may include displaying a graphical user interface on a display, the graphical user interface may include the oxygen saturation and the first message. During the first phase, the motor may be moved at a first speed and during the second phase, the motor is moved at a second speed, slower than the first speed. During the second phase, the method further may also include: measuring the oxygen saturation value in the tissue; comparing the oxygen saturation value to a second oxygen saturation range; measuring a gap distance between the anvil and the staple cartridge; comparing the measured gap distance to a gap distance range; enabling stapling if the oxygen saturation value is within the second oxygen saturation range and the measured gap distance is within the gap distance range; and outputting a second message on the display indicating inadequate blood flow if the oxygen saturation value is outside the second oxygen saturation range.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
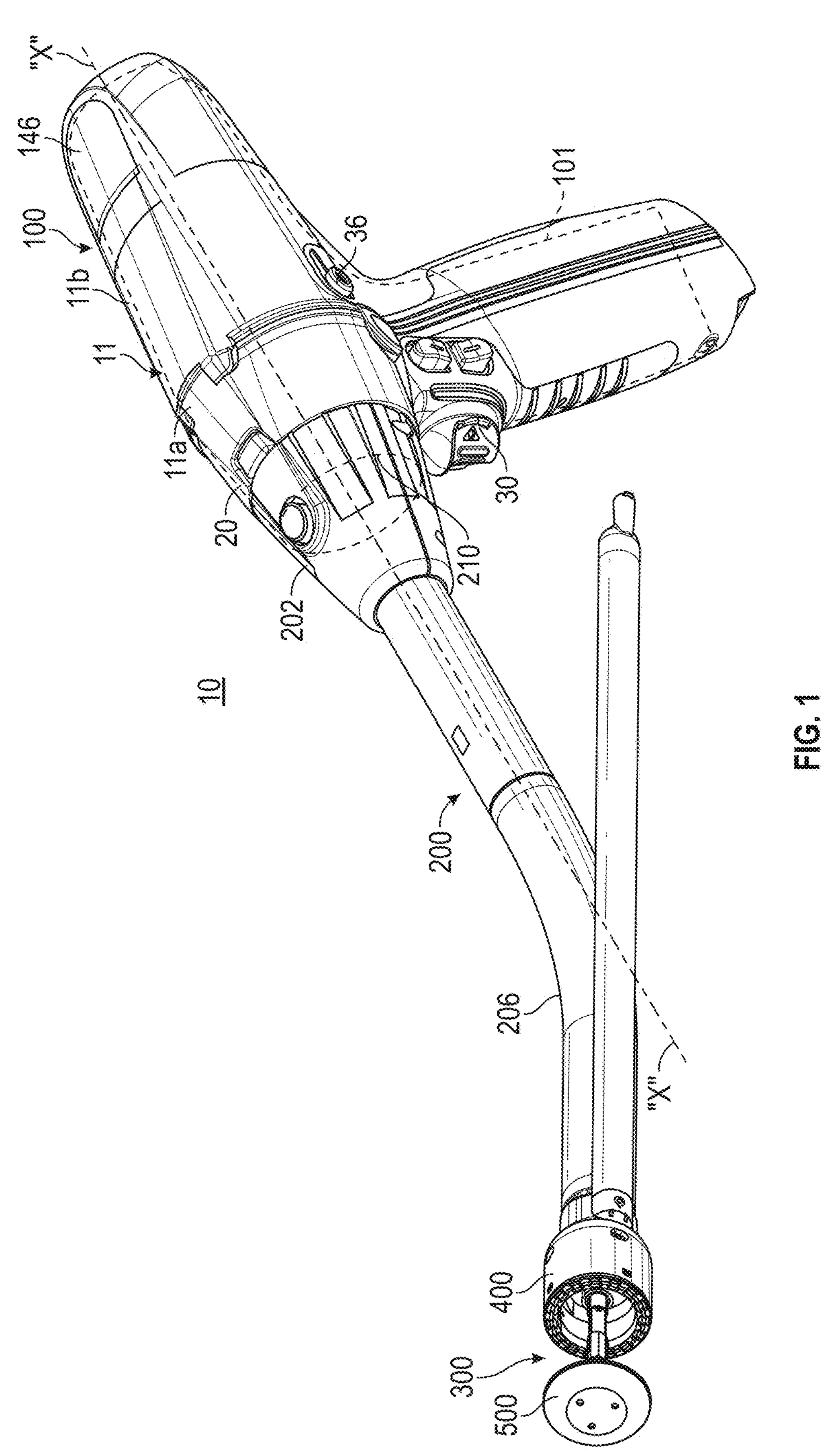
FIG. 1 is a perspective view of a powered circular stapler including a handle assembly, an adapter assembly, and an end effector, according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a powered stapler (i.e., linear or circular) having a handle assembly, an adapter assembly coupled to the handle assembly, and an end effector coupled to the adapter assembly. The stapler allows for full, independent control of three functions: clamping, stapling, and cutting. This allows certain portions of the stapler to adapt if the tissue presents a non-ideal situation.

FIG. 1 illustrates a surgical device, such as, for example, a powered circular stapler 10 for forming end-to-end anastomosis ("EEA"), including a handle assembly 100, which is configured for selective connection with an adapter assembly 200. In embodiments, the powered stapler 10 may be a linear stapler. The adapter assembly 200 is configured for selective connection with an end effector 300, which includes a reload 400 and an anvil assembly 500. The end effector 300 is configured to produce a surgical effect on tissue of a patient, namely, forming an anastomosis by connecting two portions of a structure (e.g., intestine, colon, etc.) by clamping, stapling, and cutting tissue grasped within the end effector 300.

The handle assembly 100 includes a power handle 101 and an outer shell housing 11 configured to selectively receive and encase power handle 101. The shell housing 11 includes a distal half-section 11*a* and a proximal half-section 11*b* pivotably connected to distal half-section 11*a*. When joined, distal and proximal half-sections 11*a*, 11*b* define a shell cavity therein in which power handle 101 is disposed.

While the powered circular stapler 10 is described herein as a modular device including a plurality of interconnected components, such as the handle assembly 100, the removable shell housing 11, and the adapter assembly 200, etc., the powered circular stapler 10 may be formed as an integrated device with one or more of the components being securely attached to each other, e.g., during manufacturing of the powered circular stapler.

Distal and proximal half-sections 11*a*, 11*b* of shell housing 11 are divided along a plane that traverses a longitudinal axis "X" of adapter assembly 200. Distal half-section 11*a* of shell housing 11 defines a connecting portion 20 configured to accept a corresponding drive coupling assembly 210 (FIG. 3) of adapter assembly 200. Distal half-section 11*a* of shell housing 11 supports a toggle control button 30. Toggle control button 30 is capable of being actuated in four directions (e.g., a left, right, up, and down).

Figure 2:
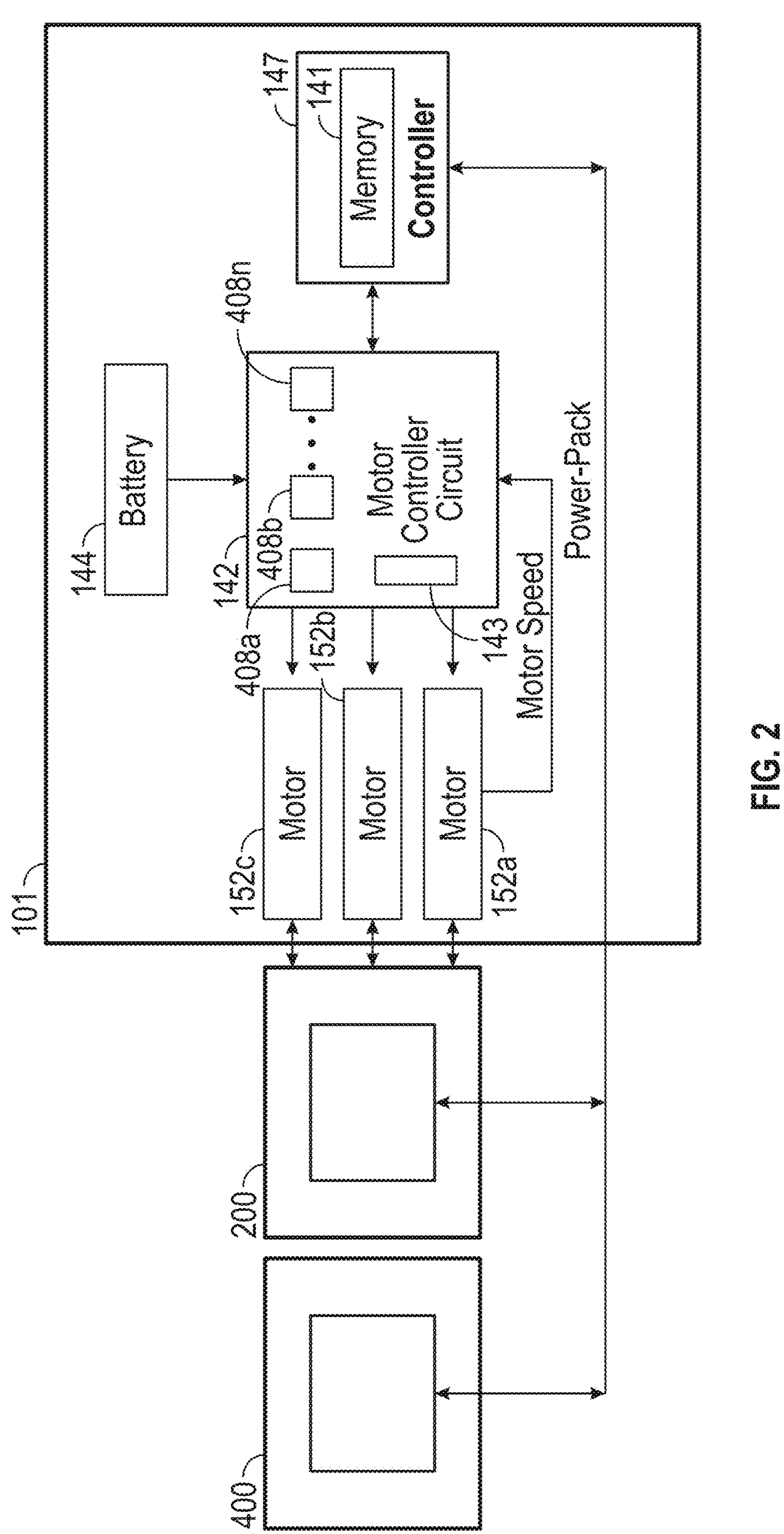
FIG. 2 is a schematic diagram of the handle assembly, the adapter assembly, and the end effector of FIG. 1.

With reference to FIGS. 1 and 2, the power handle 101 includes a circuit board 142, a rechargeable battery 144 configured to supply power to any of the electrical components of handle assembly 100, and a plurality of motors, i.e., a first motor 152*a*, a second motor 152*b*, a third motor 152*c* coupled to the battery 144. The power handle 101 also includes a display 146. In embodiments, the motors 152*a*, 152*b*, 152*c* may be coupled to any suitable power source configured to provide electrical energy to the motors 152*a*, 152*b*, 152*c*, such as an AC/DC transformer. Each of the motors 152*a*, 152*b*, 152*c* is coupled a motor controller 143 which controls the operation of the corresponding motors 152*a*, 152*b*, 152*c* including the flow of electrical energy from the battery 144 to the motors 152*a*, 152*b*, 152*c*. A main controller 147 is provided that controls the power handle 101. The main controller 147 is configured to execute software instructions embodying algorithms disclosed herein, such as clamping, stapling, and cutting algorithms which control operation of the power handle 101. The main controller 147 also processes light signals from a spectroscopy assembled as described in more detail below.

The motor controller 143 includes a plurality of sensors 408*a* . . . 408*n* configured to measure operational states of the motors 152*a*, 152*b*, 152*c* and the battery 144. The sensors 408*a-n* include a strain gauge 408*b* and may also include voltage sensors, current sensors, temperature sensors, telemetry sensors, optical sensors, and combinations thereof. The sensors 408*a*-408*n* may measure voltage, current, and other electrical properties of the electrical energy supplied by the battery 144. The sensors 408*a*-408*n* may also measure angular velocity (e.g., rotational speed) as revolutions per minute (RPM), torque, temperature, current draw, and other operational properties of the motors 152*a*, 152*b*, 152*c*. The sensor 408*a* also includes an encoder configured to count revolutions or other indicators of the motors 152*a*, 152*b*, 152*c*, which is then use by the main controller 147 to calculate linear movement of components movable by the motors 152*a*, 152*b*, 152*c*. Angular velocity may be determined by measuring the rotation of the motors 152*a*, 152*b*, 152*c* or a drive shaft (not shown) coupled thereto and rotatable by the motors 152*a*, 152*b*, 152*c*. The position of various axially movable drive shafts may also be determined by using various linear sensors disposed in or in proximity to the shafts or extrapolated from the RPM measurements. In embodiments, torque may be calculated based on the regulated current draw of the motors 152*a*, 152*b*, 152*c* at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 200 and/or the end effector 300 by counting revolutions of the motors 152*a*, 152*b*, 152*c*.

The motor controller 143 is coupled to the main controller 147, which includes a plurality of inputs and outputs for interfacing with the motor controller 143. In particular, the main controller 147 receives measured sensor signals from the motor controller 143 regarding operational status of the motors 152*a*, 152*b*, 152*c* and the battery 144 and, in turn, outputs control signals to the motor controller 143 to control the operation of the motors 152*a*, 152*b*, 152*c* based on the sensor readings and specific algorithm instructions. The main controller 147 is also configured to accept a plurality of user inputs from a user interface (e.g., switches, buttons, touch screen, etc.) coupled to the main controller 147.

The main controller 147 is also coupled to a memory 141. The memory 141 may include volatile (e.g., RAM) and non-volatile storage configured to store data, including software instructions for operating the power handle 101. The main controller 147 is also coupled to the strain gauge 408*b* of the adapter assembly 200 using a wired or a wireless connection and is configured to receive strain measurements from the strain gauge 408*b* which are used during operation of the power handle 101.

The power handle 101 includes a plurality of motors 152*a*, 152*b*, 152*c* each including a respective motor shaft (not explicitly shown) extending therefrom and configured to drive a respective transmission assembly. Rotation of the motor shafts by the respective motors functions to drive shafts and/or gear components of adapter assembly 200 in order to perform the various operations of handle assembly 100. In particular, motors 152*a*, 152*b*, 152*c* of power handle 101 are configured to drive shafts and/or gear components of adapter assembly 200 in order to selectively extend/retract a trocar member 274 (FIG. 4) of a trocar assembly 270 of adapter assembly 200, which may be fixed or removable. Extension/retraction of the trocar member 274 opens/closes end effector 300 (when anvil assembly 500 is connected to trocar member 274 of trocar assembly 270), fires an annular array of staples 423 of reload 400, and moves an annular knife 444 of reload 400.

Figure 3:
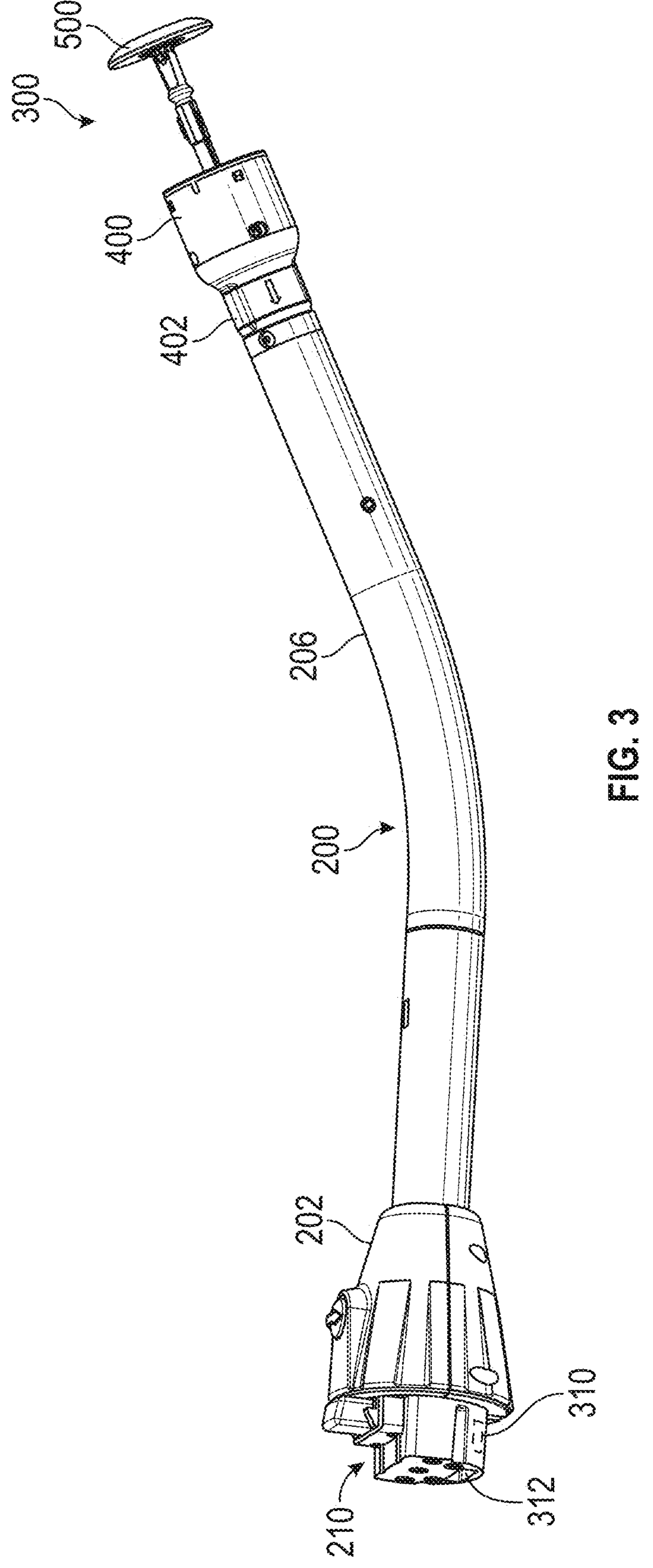
FIG. 3 is a side perspective view of the circular adapter assembly and the end effector, an annular reload and an anvil assembly, attached to the circular adapter assembly of FIG. 1 according to an embodiment of the present disclosure.
Figure 4:
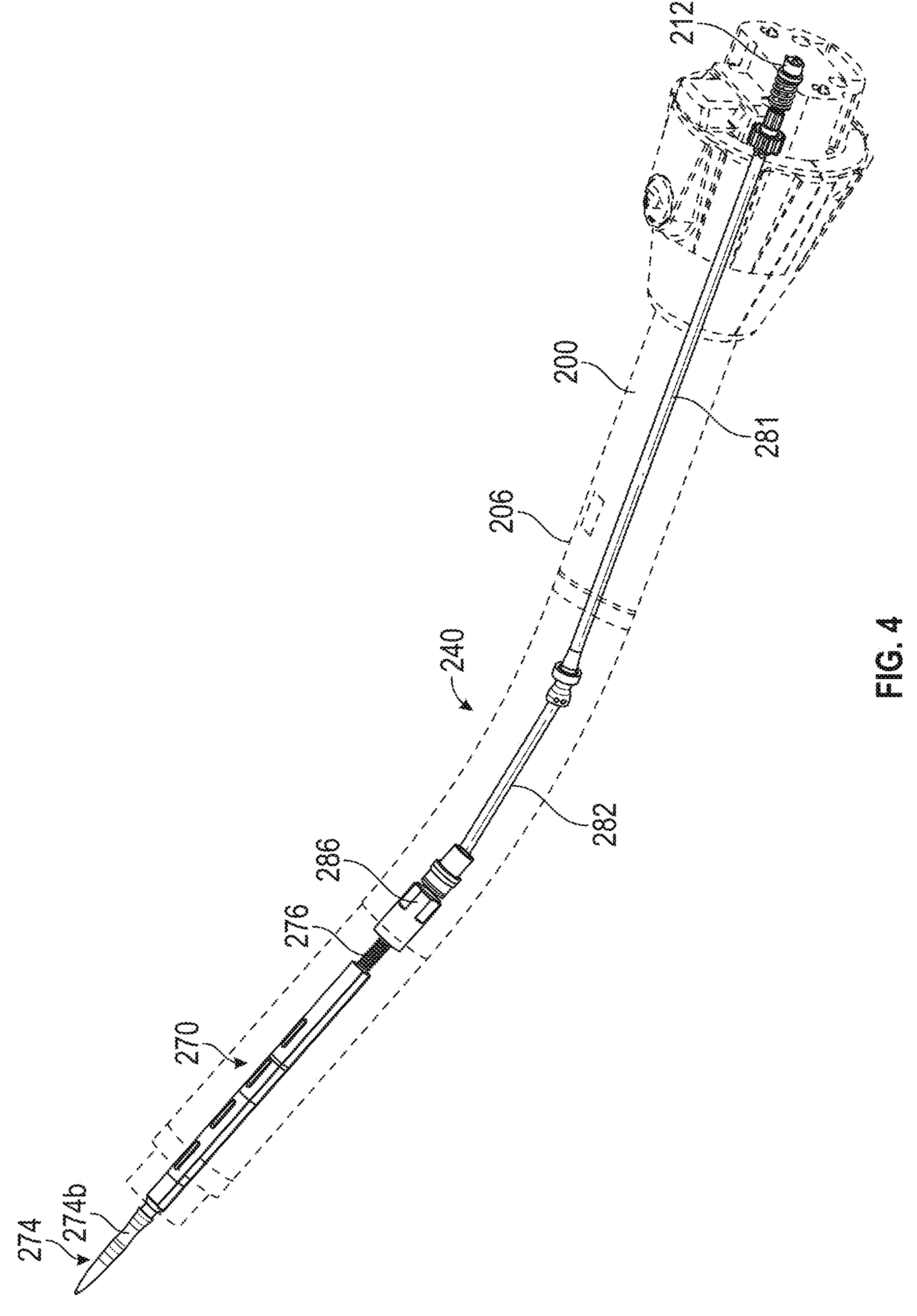
FIG. 4 is a perspective view of a clamping transmission assembly disposed within the adapter assembly of FIG. 1, shown partially in phantom.

Turning now to FIGS. 3 and 4, adapter assembly 200 includes an outer knob housing 202 and a tubular housing 206 extending from a distal end of knob housing 202. Knob housing 202 and tubular housing 206 are configured and dimensioned to house the components of adapter assembly 200. The knob housing 202 includes an electrical connector 312 and a storage device 310 coupled thereto. The storage device 310 is configured to store various operating parameters pertaining to the adapter assembly 200. Adapter assembly 200 is configured to convert rotation of coupling shafts (not explicitly shown) of handle assembly 100 into axial translations useful for operating trocar assembly 270 of adapter assembly 200, anvil assembly 500, and/or staple driver 430 or knife assembly 440 of reload 400.

Adapter assembly 200 further includes the trocar assembly 270 removably supported in a distal end of tubular housing 206. Trocar assembly 270 includes a trocar member 274 and a drive screw 276 operably received within trocar member 274 for axially moving trocar member 274 relative to tubular housing 206. A distal end 274*b* of trocar member 274 is configured to selectively engage anvil assembly 500, such that axial movement of trocar member 274, via a rotation of drive screw 276, results in a concomitant axial movement of anvil assembly 500.

With reference to FIG. 4, a clamping transmission assembly 240 includes first rotatable proximal drive shaft 212 coupled to the first motor 152*a*, a second rotatable proximal drive shaft 281, a rotatable distal drive shaft 282, and a coupling member 286, each of which is supported within the tubular housing 206 of adapter assembly 200. Clamping transmission assembly 240 functions to extend/retract trocar member 274 of trocar assembly 270 of adapter assembly 200, and to open/close the anvil assembly 500 when anvil assembly 500 is connected to trocar member 274.

Figure 5:
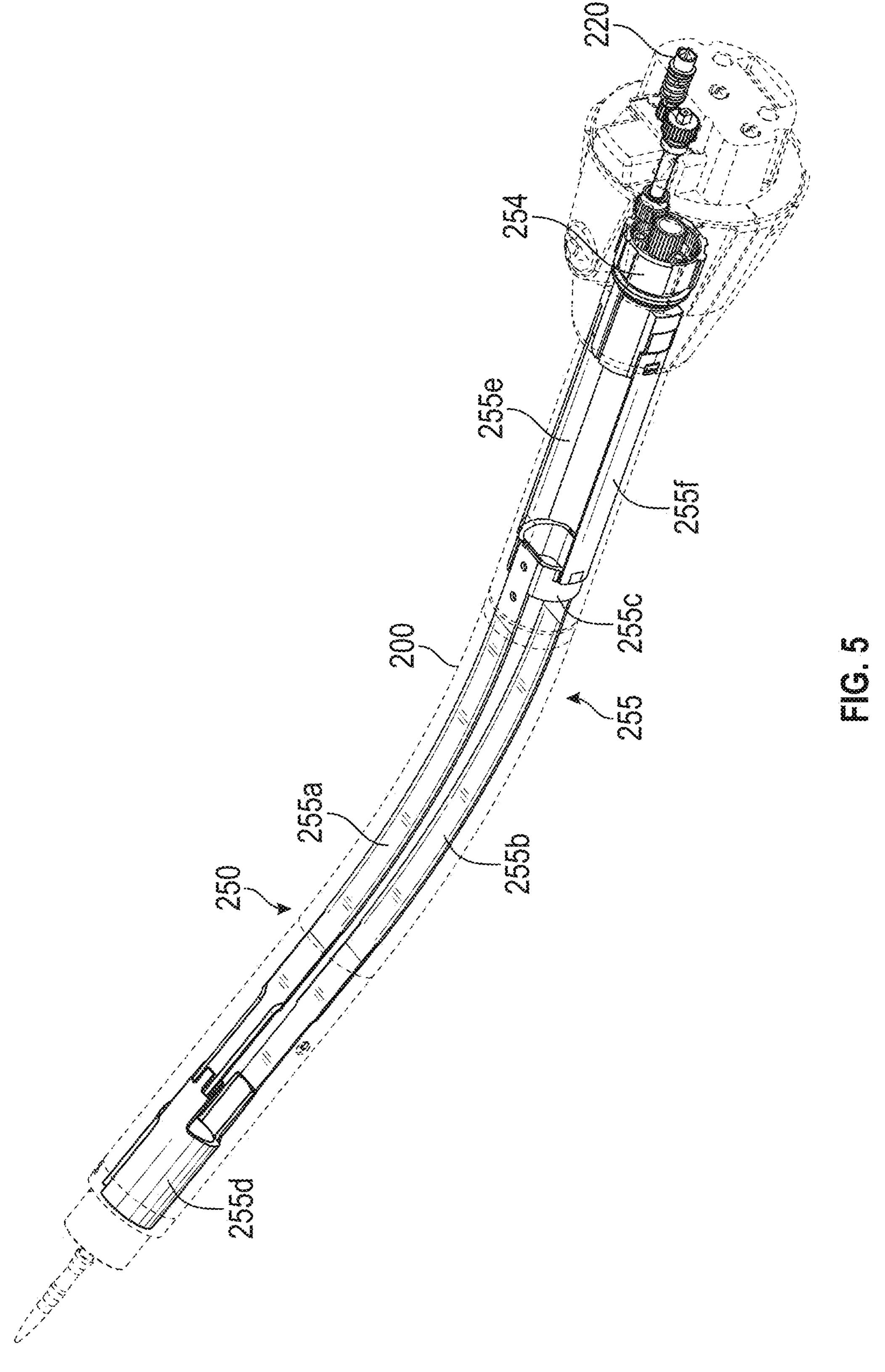
FIG. 5 is a perspective view of a stapling transmission assembly disposed within the adapter assembly of FIG. 1, shown partially in phantom.

With reference to FIG. 5, the adapter assembly 200 includes a stapling transmission assembly 250 for interconnecting the second motor 152*b* and a second axially translatable drive member of reload 400, wherein the stapling transmission assembly 250 converts and transmits a rotation of the second motor 152*b* to an axial translation of an outer flexible band assembly 255 of adapter assembly 200, and in turn, the staple driver 430 of reload 400 to fire staples 423 from the reload 400 and against anvil assembly 500.

The stapling transmission assembly 250 of adapter assembly 200 includes the outer flexible band assembly 255 secured to staple driver coupler 254. A second rotatable proximal drive shaft 220 is coupled to the second motor 152*b* and is configured to actuate that staple driver coupler 254, which converts rotational movement into longitudinal movement. Outer flexible band assembly 255 includes first and second flexible bands 255*a*, 255*b* laterally spaced and connected at proximal ends thereof to a support ring 255*c* and at distal ends thereof to a proximal end of a distal pusher 255*d*. Each of first and second flexible bands 255*a*, 255*b* is attached to support ring 255*c* and distal pusher 255*d*. Outer flexible band assembly 255 further includes first and second connection extensions 255*e*, 255*f* extending proximally from support ring 255*c*. First and second connection extensions 255*e*, 255*f* are configured to operably connect outer flexible band assembly 255 to staple driver coupler 254 of stapling transmission assembly 250.

Figure 6:
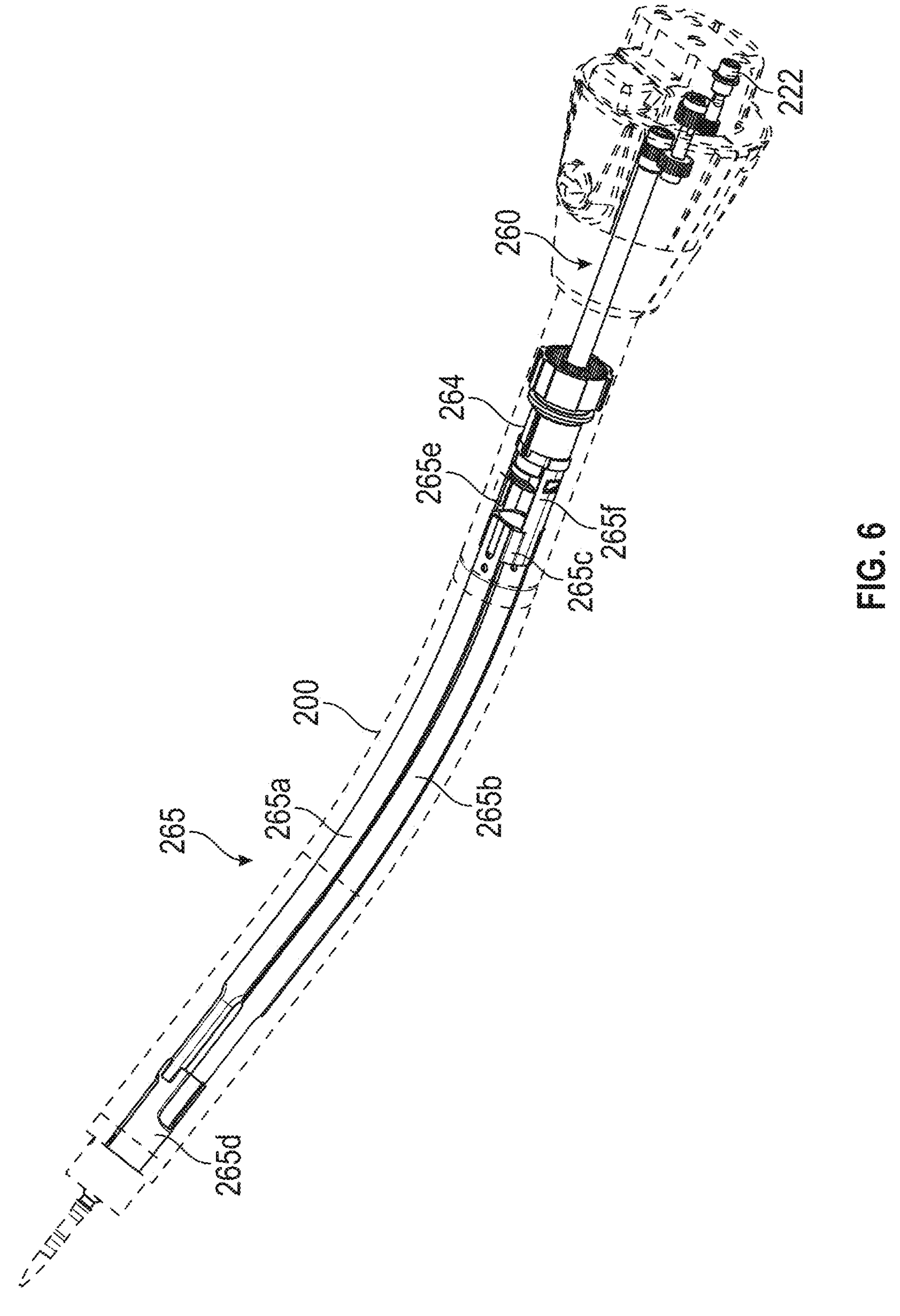
FIG. 6 is a perspective view of a cutting transmission assembly disposed within the adapter assembly of FIG. 1, shown partially in phantom.

With reference to FIG. 6, the adapter assembly 200 also includes a cutting transmission assembly 260 having a third rotatable proximal drive shaft 222 for interconnecting the third motor 152*c* and the annular knife 444 of reload 400, wherein the cutting transmission assembly 260 converts and transmits a rotation of one of the third motor 152*c* to an axial translation of an outer flexible band assembly 265 of adapter assembly 200, and in turn, a knife carrier 442 of reload 400 to advance the annular knife 444 from the reload 400 and against anvil assembly 500.

Inner flexible band assembly 265 includes first and second flexible bands 265*a*, 265*b* laterally spaced and connected at proximal ends thereof to a support ring 265*c* and at distal ends thereof to a proximal end of a support base 265*d*. Each of first and second flexible bands 265*a*, 265*b* are attached to support ring 265*c* and support base 265*d*.

Inner flexible band assembly 265 further includes first and second connection extensions 265*e*, 265*f* extending proximally from support ring 265*c*. First and second connection extensions 265*e*, 265*f* are configured to operably connect inner flexible band assembly 265 to knife driver 264 of cutting transmission assembly 260. Support base 265*d* extends distally from flexible bands 265*a*, 265*b* and is configured to connect with a knife assembly 440 of reload 400.

Figure 7:
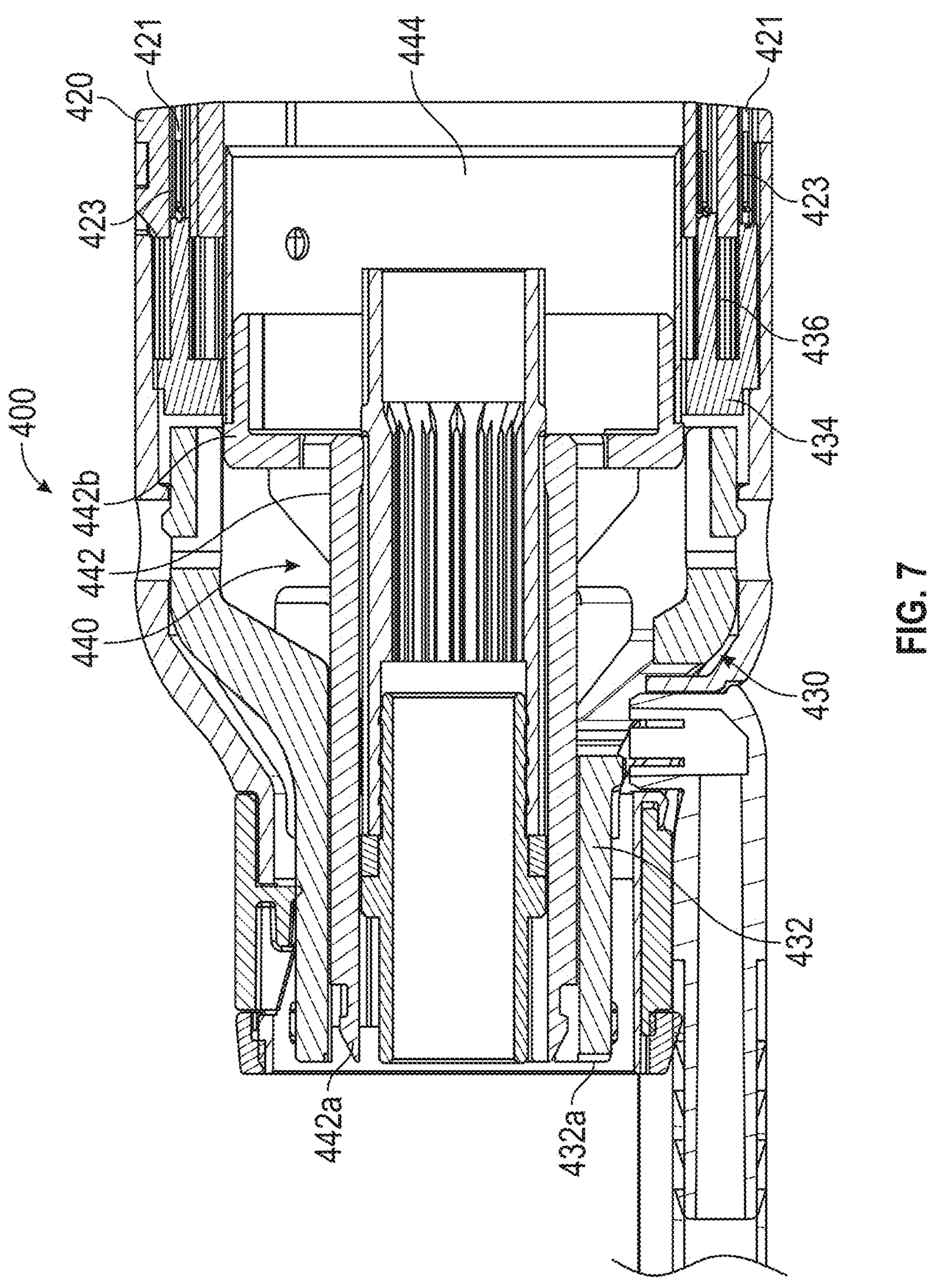
FIG. 7 is a cross-sectional view of a circular end effector of FIG. 1.

With reference to FIG. 7, staple driver 430 of reload 400 includes an annular staple cartridge 420 having a driver adapter 432 and a driver 434. A proximal end 432*a* of driver adapter 432 is configured for selective contact and abutment with distal pusher 255*d* of outer flexible band assembly 255 of stapling transmission assembly 250 of adapter assembly 200. In operation, during distal advancement of outer flexible band assembly 255, as described above, distal pusher 255*d* of outer flexible band assembly 255 contacts proximal end 432*a* of driver adapter 432 to advance driver adapter 432 and driver 434 from a first or proximal position to a second or distal position. Driver 434 includes a plurality of driver members 436 aligned with staple pockets 421 of staple cartridge 420 for contact with staples 423. Accordingly, advancement of driver 434 relative to staple cartridge 420 causes ejection of the staples 423 from staple cartridge 420.

The knife assembly 440 of the reload 400 includes a knife carrier 442 and an annular knife 444 secured about a distal end 442*b* of knife carrier 442. A proximal end 442*a* of knife carrier 442 is configured to engage the support base 265*d* of inner flexible band assembly. In operation, during distal advancement of inner flexible band assembly 265, support base 265*d* of inner flexible band assembly 265 connects with proximal end 442*a* of knife carrier 442 to advance knife carrier 442 and annular knife 444 from a first or proximal position to a second or advanced position to cause the cutting of tissue disposed between staple cartridge 420 and anvil assembly 500.

Forces during an actuation of trocar member 274, closing of end effector 300 (e.g., a retraction of anvil assembly 500 relative to reload 400), ejecting staples 423 from the reload 400, and advancement of the knife assembly 440 may be measured by the strain gauge 408*b* in order to monitor and control various processes, such as firing of staples 423 from reload 400; monitor forces during a firing and formation of the staples 423 as the staples 423 are being ejected from reload 400; optimize formation of the staples 423 (e.g., staple crimp height) as the staples 423 are being ejected from reload 400 for different indications of tissue; and monitor and control a firing of the annular knife of reload 400.

Figure 8:
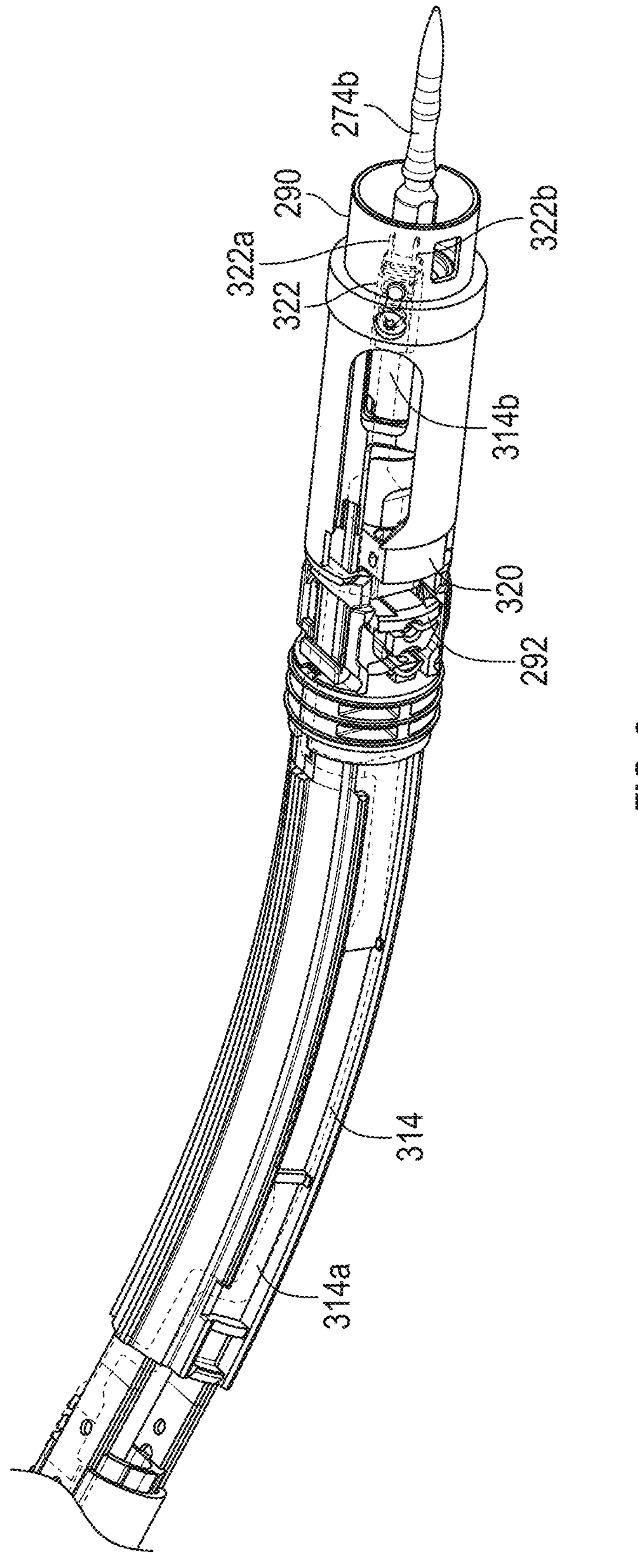
FIG. 8 is a perspective view of the circular adapter assembly, shown partially disassembled, with a strain gauge assembly.

With reference to FIG. 8, the strain gauge 408*b* of adapter assembly 200 is disposed within a strain gauge housing 320. The strain gauge 408*b* measures and monitors the retraction of trocar member 274 as well as the ejection and formation of the staples 423 from the reload 400. During the closing of end effector 300, when anvil assembly 500 contacts tissue, an obstruction, a tissue-contacting surface of the reload 400, staple ejection, or the like, a reaction force is exerted on anvil assembly 500 which is in a generally distal direction. This distally directed reaction force is communicated from anvil assembly 500 to the strain gauge 408*b*. The strain gauge 408*b* then communicates signals to main controller 147 of power handle 101 of handle assembly 100. Graphics (FIG. 8) are then displayed on the display 146 of handle assembly 100 to provide the user with real-time information related to the status of the firing of handle assembly 100.

The trocar assembly 270 is axially and rotationally fixed within tubular housing 206 of adapter assembly 200. With reference to FIG. 8, adapter assembly 200 includes a support block 292 fixedly disposed within tubular housing 206. The strain gauge housing 320 is disposed between the support block 292 and a connector sleeve 290. The reload 400 is removably coupled to the connector sleeve 290.

In operation, strain gauge 408*b* of adapter assembly 200 measures and monitors the retraction of trocar member 274, which passes through the strain gauge 408*b*. The strain gauge 408*b* of adapter assembly 200 also measures and monitors ejection of the staples 423 from the reload 400, since the first and second flexible bands 255*a*, 255*b* also pass through the strain gauge 408*b*. During clamping, stapling, and cutting, a reaction force is exerted on anvil assembly 500 and the reload 400, which is communicated to support block 292, which then communicates the reaction force to a strain sensor of the strain gauge 408*b*.

Strain sensor of strain gauge 408*b* may be any device configured to measure strain (a dimensionless quantity) on an object that it is adhered to (e.g., support block 292), such that, as the object deforms, a metallic foil of the strain sensor is also deformed, causing an electrical resistance thereof to change, which change in resistance is then used to calculate loads experienced by trocar assembly 270. Strain gauge 408*b* provides closed-loop feedback to a firing/clamping load exhibited by first, second and third force/rotation transmitting/converting assemblies.

Strain sensor of strain gauge 408*b* then communicates signals to main controller 147. Graphics are then displayed on display 146 of handle assembly 100 to provide the user with real-time information related to the status of the firing of handle assembly 100. Strain gauge 408*b* is also electrically connected to the electrical connector 312 (FIG. 3) via a wiring harness 314 having a proximal portion 314*a*. The wiring harness 314 may be any ribbon cable or any other suitable cable or wiring assembly. A distal portion 314*b* of the wiring harness 314 is coupled to a distal connector 322 which is supported in connector sleeve 290. Distal connector 322 is configured to selectively mechanically, electrically and/or optically connect to the reload 400 when reload 400 is connected to adapter assembly 200. In particular, the connector 322 may include a plug having a pair of contacts 322*a* and 322*b*. The connector 322 is also configured to couple to the storage device 402.

For further details regarding the construction and operation of the circular stapler and its components, reference may be made to International Application Publication No. PCT/US2019/040440, filed on Jul. 3, 2019, the entire contents of which being incorporated by reference herein.

The reload 400 includes a storage device 402 and the circular adapter assembly 200 also includes a storage device 310 (FIG. 4). The storage devices 402 and 310 include non-volatile storage medium (e.g., EEPROM) that is configured to store any data pertaining to the reload 400 and the circular adapter assembly 200, respectively, including but not limited to, usage count, identification information, model number, serial number, staple size, stroke length, maximum actuation force, minimum actuation force, factory calibration data, and the like. In embodiments, the data may be encrypted and is only decryptable by devices (e.g., main controller 147) having appropriate keys. The data may also be used by the main controller 147 to authenticate the circular adapter assembly 200 and/or the reload 400. The storage devices 402 and 310 may be configured in read only or read/write modes, allowing the main controller 147 to read as well as write data onto the storage device 402 and 310.

Figure 9:
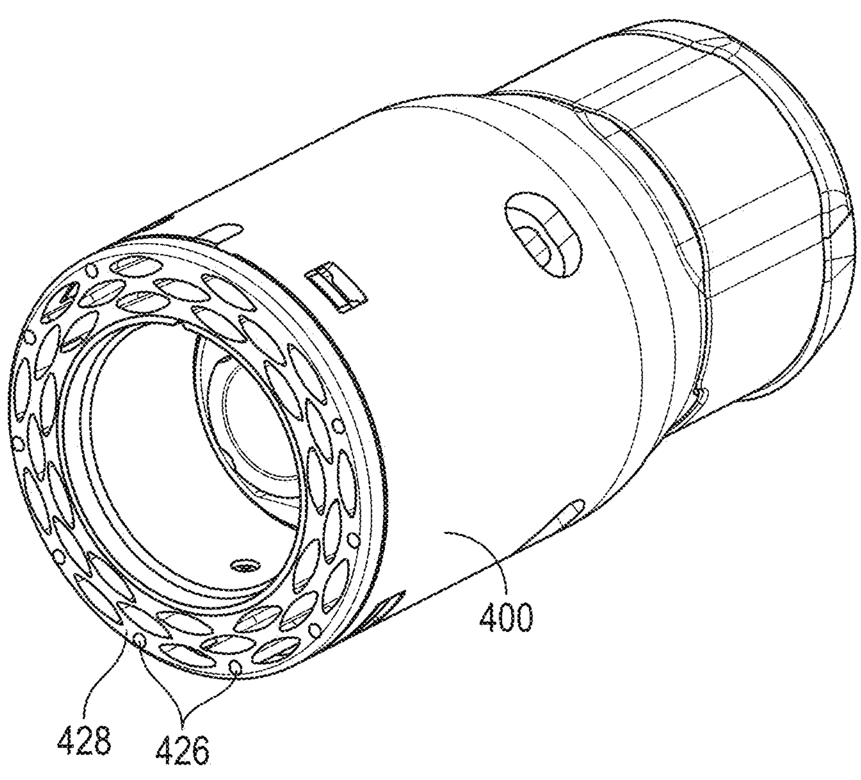
FIG. 9 is a perspective view of a reload of the end effector of FIG. 1 according to an embodiment of the present disclosure.
Figure 10:
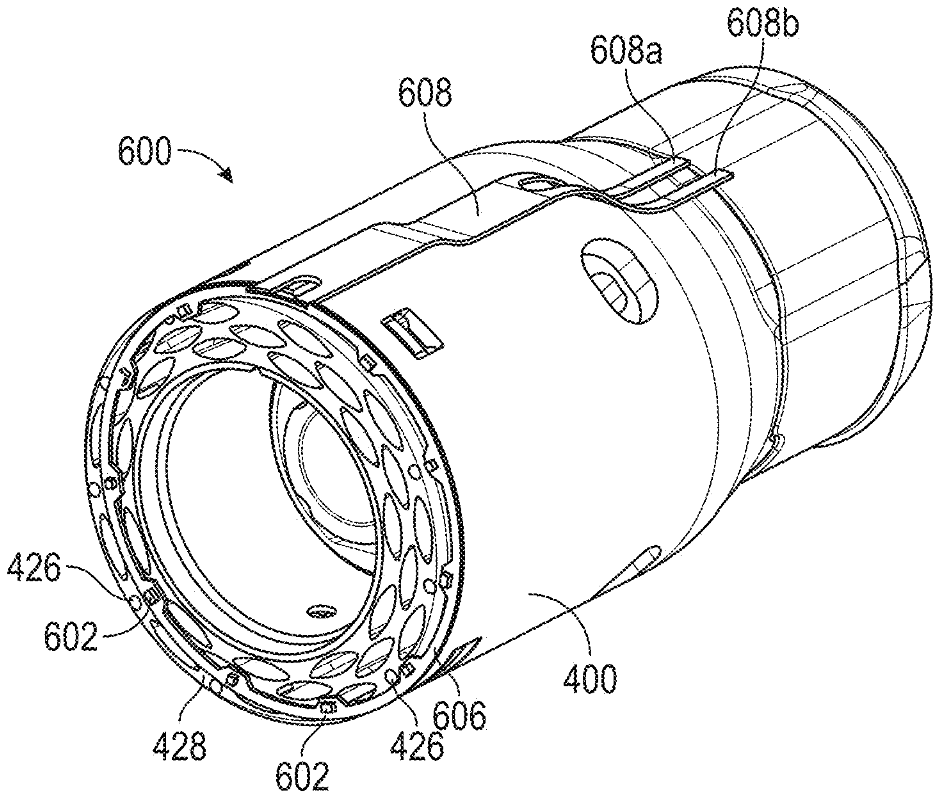
FIG. 10 is a perspective, partially disassembled view of a circular the end effector of FIG. 1 according to an embodiment of the present disclosure.

With reference to FIGS. 9 and 10, a spectroscopy assembly or NIRS system 600 is shown. The NIRS system 600 includes a plurality of light sources 602, which may be laser diodes, configured to output NIR light which may be in the range of about 700 nm to about 900 nm. In embodiments, the light sources 602 may also output light in the red and NIR range, which may be in the range of from about 650 nm to about 850 nm. The light may be outside the visible spectrum and is suitable for imaging oxygenation of tissue (i.e., oxygen saturation or $SpO_2$), that is primarily absorbed by oxyhemoglobin and/or deoxyhemoglobin. Measuring oxygenation is directly related to blood perfusion, knowledge of which is useful during all phases of the procedure, e.g., clamping, stapling, and cutting.

The NIRS system 600 operates by transmitting light from the light sources 602 into tissue interposed between reload 400 and the anvil assembly 500 and detecting light reflected therefrom at a plurality of photodetectors 604. The photodetectors 604 may be photodiodes or any other suitable light sensitive element configured to operate in the spectrum of the light sources 602. The light sources 602 and the photodetectors 604 are interspersed along an outer perimeter of the reload 400. In particular, the light sources 602 and the photodetectors 604 are disposed on a ring-shaped flexible circuit 606 which provides electrical connections, e.g., traces, for each of the light sources 602 and the photodetectors 604. The flexible circuit 606 may be disposed at any location of the reload 400, e.g., inward from the periphery. The flexible circuit 606 is disposed within the staple cartridge 420, which includes a plurality of openings 426 defined in a stapling surface 428. The openings 426 may be aligned with each of the light sources 602 and the photodetectors 604 to enable light transmission. The openings 426 may have any suitable depth, e.g., from about 0.1 mm to about 2 mm and prevent outside light from hitting the photodetectors 604.

The flexible circuit 606 also includes a lead 608 having a pair of connectors 608*a* and 608*b* that are configured to couple to the contacts 322*a* and 322*b* of the connector 322 (FIG. 8). The connector 322 may be electrical or optical and may include A/D converters to convert analog signal from the photodetectors 604 for transmission along the wiring harness 314 to the main controller 147. In embodiments, A/D converters may be disposed in the handle assembly 100.

The main controller 147 is configured to process the signals from the photodetectors 604 to determine a level of perfusion in the stapled tissue. In embodiments, the photodetectors 604 may be individually addressable so that perfusion may be assessed by the main controller 147 at each location of the photodetector 604. In embodiments, the main controller 147 may display a graphical user interface (GUI) on the display 146 indicating a degree of perfusion and/or whether perfusion is at a desired level corresponding to a successful stapling operation. The GUI may be displayed on any other display present in the operating room. The GUI may use color-coded indicators, e.g., red, yellow, green, to indicate perfusion assessment. In embodiments with individually addressable photodetectors 604, perfusion for each may be displayed separately, e.g., in a ring segmented into regions corresponding to each of the addressable photodetectors 604.

Prior to operation of the powered circular stapler 10, the power handle 101 is enclosed within the shell housing 11 the adapter assembly 200 is coupled to handle assembly 100. After attachment of circular adapter assembly 200, handle assembly 100 initially verifies that circular adapter assembly 200 is coupled thereto by establishing communications with the storage device 310 of the circular adapter assembly 200 and authenticates circular adapter assembly 200. The data (e.g., usage count) stored on the storage device 310 is encrypted and is authenticated by the power handle 101 prior to determining whether the usage count stored on the storage device 310 exceeds the threshold (e.g., if the adapter assembly 200 has been previously used). Power handle 101 then performs verification checks (e.g., end of life checks, trocar member 274 missing, etc.) and calibrates circular adapter assembly 200 after the handle assembly 100 confirms that the trocar member 274 is attached.

The user commences a surgical procedure by positioning the adapter assembly 200, including the trocar member 274 and the anvil assembly 500, within the colorectal or upper gastrointestinal region. The user presses the toggle control button 30 to extend the trocar member 274 until it pierces tissue. After extension of the trocar member 274, the anvil assembly 500 that was previously positioned by surgeon is attached to the trocar member 274 and the user begins the clamping process on the tissue interposed between reload 400 and the anvil assembly 500 by pressing on the bottom portion of the toggle control button 30.

The powered circular stapler 10 may also initiate an optical verification or baseline test prior to commencing the stapling procedure. The clamping process may include controlled tissue compression until a desired threshold is reached. Once tissue is compressed, the user may initial the stapling process by pressing the toggle control button 30. In embodiments, the baseline test may occur after the tissue is compressed.

In embodiments, the stapling process may be commenced automatically once tissue compression is confirmed by the main controller 147. After stapling is completed, cutting is initiated automatically or by pressing the toggle control button 30, at which point the main controller 147 initiates a perfusion check which includes energizing the light sources 602 to illuminate the stapled tissue. The reflected or backscattered light is received by the photodetectors 604, which provide the detected signal to the main controller 147, which then compares the signals to a perfusion threshold. The main controller 147 may also display the level of perfusion on the display 146. In embodiments, perfusion assessment may be performed at other stages of the procedure, including at its conclusion, i.e., after stapling.

Figure 11:
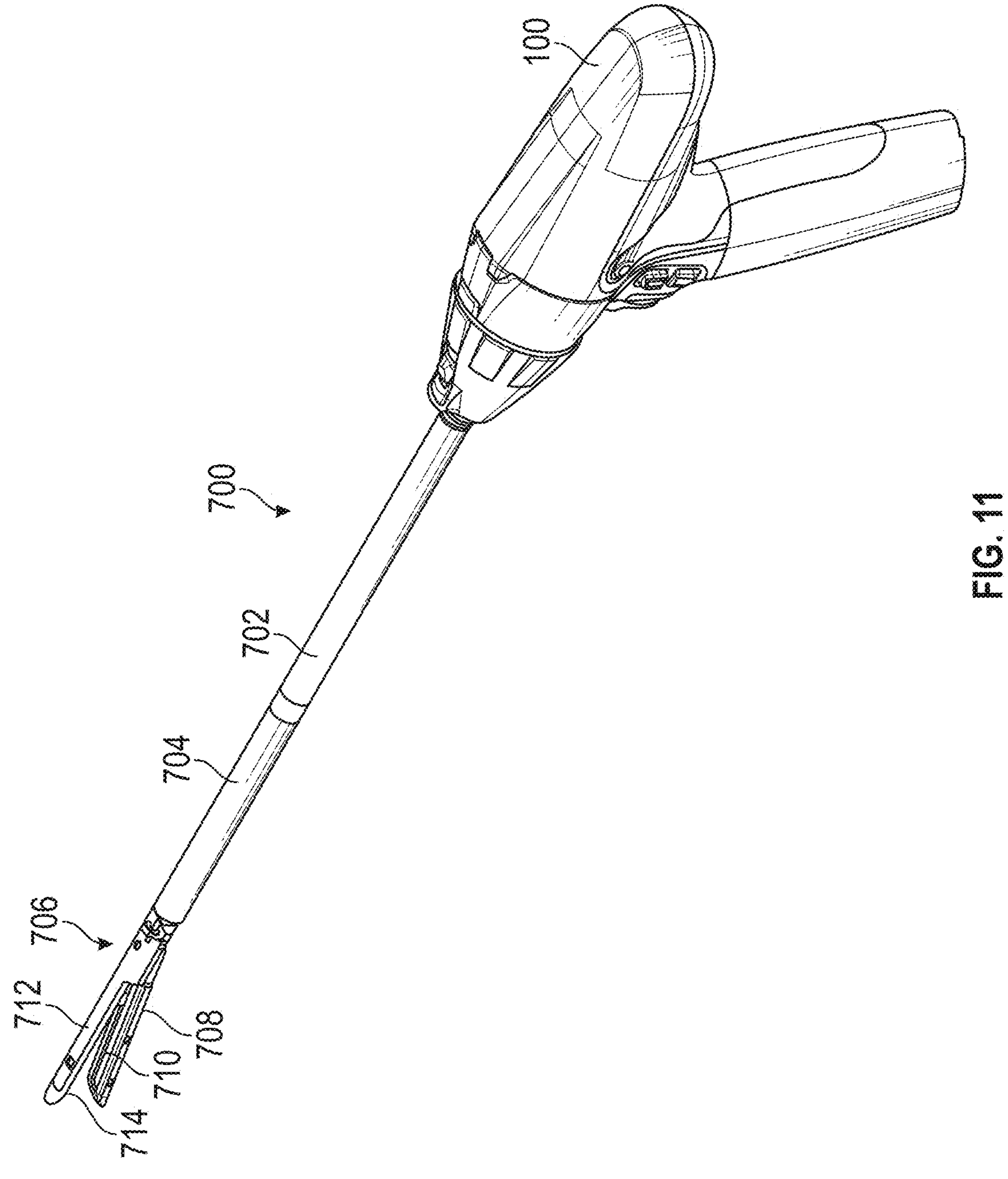
FIG. 11 is a perspective view of a powered linear stapler including a handle assembly, an adapter assembly, and an end effector, according to an embodiment of the present disclosure.

FIG. 11 shows a linear powered stapler 700, which may share a common power platform with the powered circular stapler 10, i.e., a handle assembly 100 including one or more motors, a power source, a main controller, storage device, transmitter/receiver, etc. The stapler 700 also includes a linear adapter 702 configured to connect the handle assembly 100 to a loading unit 704 including an end effector 706 having a first jaw 708 having a staple cartridge 710 and a second jaw 712 having an anvil 714. The linear adapter 702 includes various mechanical linkages coupling the end effector 706 with the handle assembly 100 enabling actuation of the end effector 706 to perform various functions, e.g., clamp, staple, cut. For further details regarding the construction and operation of the linear stapler components, reference may be made U.S. Pat. No. 9,839,425, filed on Mar. 30, 2015, the entire contents of which being incorporated by reference herein.

Figures 12, 13:
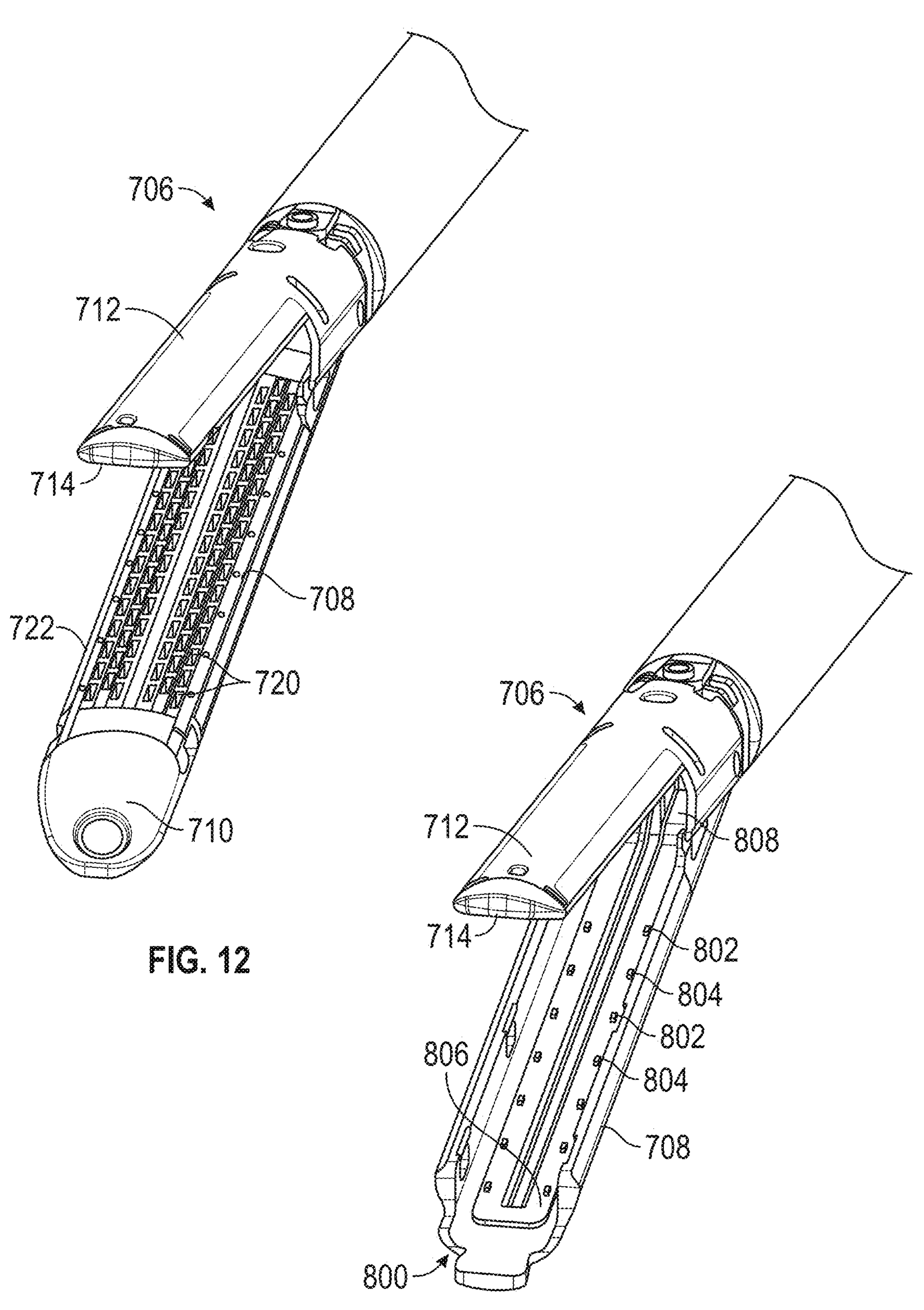
FIG. 12 is a perspective view of the end effector of FIG. 11 according to an embodiment of the present disclosure.
FIG. 13 is a perspective, partially disassembled view of the end effector of FIG. 11 according to an embodiment of the present disclosure.

With reference to FIGS. 12 and 13, another embodiment of the spectroscopy assembly or NIRS system 800 is shown, which is substantially similar in functionality to the NIRS system 600 but is different in shape, i.e., linear vs annular. The NIRS system 800 includes a plurality of light sources 802, which may be laser diodes, configured to output NIR light which may be in the range of about 700 nm to about 900 nm. In embodiments, the light sources 802 may also output light in the red and NIR range, which may be in the range of from about 650 nm to about 850 nm.

The NIRS system 800 operates in the same manner as the NIRS system 600 by transmitting light from the light sources 802 into tissue interposed between first jaw 708 and the second jaw 712 and detecting light reflected or backscattered therefrom at a plurality of photodetectors 804. The photodetectors 804 may be photodiodes or any other suitable light sensitive element configured to operate in the spectrum of the light sources 802.

The NIRS system 800 may be disposed in one or both of the first jaw 708 and the second jaw 712. The light sources 802 may be disposed in one of the jaws 708 and 712 with the photodetectors 804 being disposed in another of the jaws 708 and 712. In further embodiments, each of the jaws may include the light sources 802 and photodetectors 804 as shown in FIG. 13.

The light sources 802 and the photodetectors 804 may be interspersed along an outer perimeter of the first jaw 708. In particular, the light sources 802 and the photodetectors 804 are disposed on a linear-shaped flexible circuit 806 which provides electrical connections, e.g., traces, for each of the light sources 802 and the photodetectors 804. The flexible circuit 806 may be disposed at any location of the first jaw 708, e.g., inward from the periphery. The flexible circuit 806 is disposed within the first jaw 708 and the staple cartridge 710 includes a plurality of openings 720 defined in a stapling surface 722. The openings 720 may be aligned with each of the light sources 802 and the photodetectors 804 to enable light transmission. The openings 720 may have any suitable depth, e.g., from about 0.1 mm to about 2 mm and prevent outside light from hitting the photodetectors 804.

The flexible circuit 806 also includes a lead 808 having a pair of electrical contacts 808*a* and 808*b* that are configured to optically or electrically couple to the contacts (not shown) of the linear adapter 702. The linear adapter 702 or the handle assembly 100 may include A/D converters to convert analog signal from the photodetectors 804 for transmission along a wiring harness to the main controller 147. The main controller 147 is configured to process the signals from the photodetectors 804 to determine a level of perfusion in the stapled tissue. In embodiments, the photodetectors 804 may be individually addressable so that perfusion may be assessed by the main controller 147 at each location of each photodetector 804. In embodiments, the main controller 147 may display a graphical user interface (GUI) on the display 146 indicating a degree of perfusion and/or whether perfusion is at a desired level corresponding to a successful stapling operation. The GUI may be displayed on any other display present in the operating room. The GUI may use color-coded indicators, e.g., red, yellow, green, to indicate perfusion assessment. In embodiments with individually addressable photodetectors 804, perfusion for each may be displayed separately, e.g., in a ring segmented into regions corresponding to each of the addressable photodetectors 804.

During use, the linear powered stapler 700 is advanced to a surgical site, e.g., through an access port. The user presses the toggle control button 30 to commence the stapling process, which initially clamps tissue between the first and second jaws 708 and 712. A drive rod (e.g., I-beam) may engage the first and second jaws 708 and 712 to approximate the jaws 708 and 712 toward each other.

After clamping is completed, the main controller 147 may initiate an optical verification or baseline test prior to commencing the stapling procedure. During cutting and stapling, the drive rod is continuously advanced, which pushes an ejector (e.g., sled) along with a knife blade to cut and staple tissue until the ejector and/or knife reach the mechanical limit, e.g., distal end of the first and second jaws 708 and 712. Thereafter, the drive rod is retracted, which retracts the knife, while the sled may remain at the distal position. As the drive rod is retracted further, the first and second jaws 708 and 712 are unclamped.

Prior to unclamping, the main controller 147 initiates a perfusion check which includes energizing the light sources 802 to illuminate the clamped tissue. The reflected or backscattered light is received by the photodetectors 804, which provide the detected signal to the main controller 147, which then compares the signals to a perfusion threshold. The main controller 147 may also display the level of perfusion on the display 146. In embodiments, perfusion assessment may be performed at other stages of the procedure, i.e., after initial clamping and prior to stapling.

Figure 14:
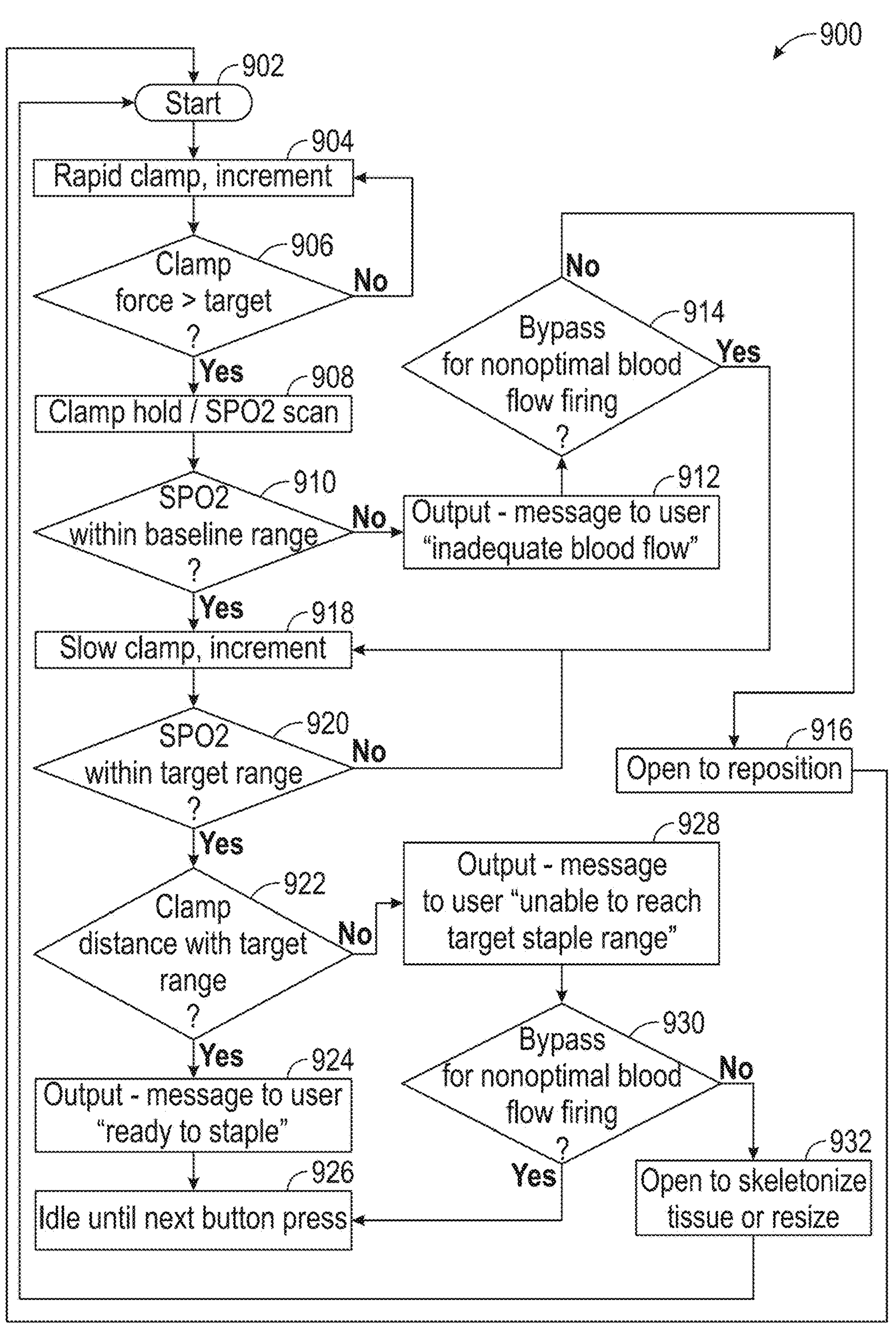
FIG. 14 is a flow chart of a method for real-time tissue perfusion assessment during clamping according to an embodiment of the present disclosure.

FIG. 14 shows a flow chart of a method 900 for real-time tissue perfusion assessment during clamping. The method may be embodied as software instructions stored in memory 141, which are executable by a processor, e.g., main controller 147. The method 900 is described with respect to the powered circular stapler 10 but may also be performed using the linear powered stapler 700 with modification to accommodate the surgical steps, e.g., as there is no need for trocar deployment.

At step 902, the user commences a surgical procedure by positioning the adapter assembly 200, including the trocar member 274 and the anvil assembly 500, within the colorectal or upper gastrointestinal region. The user presses the toggle control button 30 to extend the trocar member 274 until it pierces tissue. During operation, the anvil assembly 500 (after being positioned by surgeon at the tissue site where anastomosis is being performed) is attached to the trocar member 274 and the user begins the clamping process on the tissue interposed between reload 400 and the anvil assembly 500 by pressing on the bottom of the toggle control button 30. After extension of the trocar member 274, the anvil assembly 500 that was previously positioned by the surgeon is attached to the trocar member 274. The surgeon then begins the clamping process on the tissue interposed between reload 400 and the anvil assembly 500 by pressing on the bottom portion of the toggle control button 30.

During clamping, the anvil assembly 500 is retracted toward the reload 400 until reaching a preset, fully clamped position. The preset clamped position varies for each of the different types of reloads (e.g., the distance is about 29 mm for 25 mm reloads). While clamping, the strain gauge 408*b* continuously provides measurements to the main controller 147 on the force imparted on the trocar member 274 as it moves the anvil assembly 500 to clamp tissue between the anvil assembly 500 and the reload 400.

At step 904, the anvil assembly 500 is retracted, i.e., moved proximally, from a fully open position at a first speed (e.g., rapid) towards the reload 400. This is done in response to the user pressing the toggle control button 30. The anvil assembly 500 is retracted until reaching a target clamp force, which may be from about 80 lbs to about 150 lbs, which in embodiments may be about 100 lbs. This check is performed by the controller 147 continuously at step 906 while the anvil assembly 500 is retracted.

Upon reaching the target clamp force, at step 908, the controller 147 stops the clamping process and the anvil assembly 147 is held in place (i.e., unmoved). During this phase, the main controller 147 performs a perfusion or oxygen saturation check which includes energizing the light sources 602 to illuminate the clamped tissue and measure oxygen saturation. The reflected or backscattered light is received by the photodetectors 604, which provide the detected signal to the main controller 147, which then compares the signals to a first (i.e., minimum) oxygen saturation threshold or a first (i.e., baseline) range at step 910.

If the measured oxygen saturation is outside the first oxygen saturation range or below the first oxygen saturation threshold, then at step 912 the controller 147 outputs a visual or audio prompt indicating the oxygen saturation is too low. For example, the prompt may be output on the display 146 stating "inadequate blood flow." In response to the prompt, at step 914 the stapler 10 may be operated to bypass the prompt for nonoptimal blood flow firing. Alternatively, the stapler 10 may be opened at step 916, i.e., the anvil assembly 500 is advanced to unclamp tissue and to restart the clamping process.

If the measured oxygen saturation is within the first oxygen saturation range or above the first oxygen saturation threshold, then at step 918 clamping is resumed. This may also be performed in response to the bypass selection. During this step, the anvil assembly 500 is retracted, i.e., moved proximally, from the last stoppage position towards at a second speed (e.g., slower than the first speed) towards the reload 400. This is done in response to the user continually pressing the toggle control button 30.

During clamping, tissue oxygen saturation is periodically measured at step 920. This may be done by incrementally decreasing the clamping distance and performing an oxygen saturation check. The main controller 147 performs a perfusion or oxygen saturation check by energizing the light sources 602 to illuminate the clamped tissue and measure oxygen saturation. The reflected or backscattered light is received by the photodetectors 604, which provide the detected signal to the main controller 147, which then compares the signals to a second (i.e., target) oxygen saturation threshold or a second (i.e., target) range at step 920. The second range may be nested within the first range or the second threshold may be above the first threshold. The step 920 is repeated until measured oxygen saturation is within the second oxygen saturation range or above the second oxygen saturation threshold.

In addition to checking oxygen saturation, the controller 147 also checks whether desired clamping distance has been reached. This may be done by incrementally decreasing the clamping distance and performing a position check on the anvil assembly 500. At step 922, at each increment, the controller 147 compares the current gap distance (i.e., separation between the anvil assembly 500 and the reload 400) to a target gap range or gap threshold.

At step 924, the controller 147 outputs a visual or audio alert indicating the powered stapler 10 may proceed to stapling. This is done if both gap and oxygen saturation and gap distance conditions of steps 920 and 922, respectively, are satisfied. Thus, if the gap distance is within the target gap range or is less than the gap threshold (from step 922) and the oxygen saturation is within the second oxygen saturation range or exceeds the second oxygen saturation threshold (from step 920), then the controller 147 outputs a visual or audio prompt indicating that stapling may be performed. For example, the prompt may be output on the display 146 stating "ready to staple." In response to the prompt, at step 926 the stapler 10 may be operated by pressing the control button 30 to commence the stapling operation by ejecting the staples from the reload 400.

At step 928, the controller 147 outputs a visual or audio alert indicating the powered stapler 10 may not proceed to stapling. This is done if the gap distance is outside the target gap range or is larger than the gap threshold (from step 922) and/or if the oxygen saturation is outside the second oxygen saturation range or is below the second oxygen saturation threshold (from step 920). The controller 147 outputs a visual or audio prompt indicating that stapling may not be performed. For example, the prompt may be output on the display 146 stating "unable to reach target staple range." In response to the prompt, at step 930 the stapler 10 may be operated to bypass the prompt for nonoptimal blood flow firing, where the stapler may be operated to staple tissue as described with respect to step 926. Alternatively, the stapler 10 may be opened at step 932, i.e., the anvil assembly 500 is advanced to unclamp tissue, to skeletonize tissue and/or select a different size reload 400.

It will be understood that various modifications may be made to the embodiments of the presently disclosed staplers. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical stapler comprising:

a motor;

a staple cartridge including a plurality of staples;

an anvil movable by the motor relative to the staple cartridge and configured to compress tissue therebetween;

a spectroscopy assembly including a plurality of light sources and a plurality of photodetectors interspersed among the plurality of light sources; and a controller coupled to the spectroscopy assembly, the controller configured to:

activate the motor during a first phase of clamping to move the anvil to clamp tissue between the anvil and the staple cartridge;

measure an oxygen saturation value in the tissue using the spectroscopy assembly;

compare the oxygen saturation value to a first oxygen saturation range;

output a first message indicating inadequate blood flow if the oxygen saturation value is outside the first oxygen saturation range; and activate the motor during a second phase of the clamping to move the anvil to further clamp the tissue between the anvil and the staple cartridge if the oxygen saturation value is within the first oxygen saturation range.

2. The surgical stapler according to claim 1, further comprising a display configured to show a graphical user interface, wherein the controller is further configured to output the oxygen saturation value and the first message on the graphical user interface.

3. The surgical stapler according to claim 2, wherein during the first phase, the motor is moved at a first speed.

4. The surgical stapler according to claim 3, wherein during the second phase, the motor is moved at a second speed that is slower than the first speed.

5. The surgical stapler according to claim 4, wherein during the second phase, the controller is further configured to:

measure the oxygen saturation value in the tissue; and compare the oxygen saturation value to a second oxygen saturation range.

6. The surgical stapler according to claim 5, wherein during the second phase, the controller is further configured to:

measure a gap distance between the anvil and the staple cartridge; and compare the measured gap distance to a gap distance range.

7. The surgical stapler according to claim 6, wherein during the second phase, the controller is further configured to enable stapling if the oxygen saturation value is within the second oxygen saturation range and the measured gap distance is within the gap distance range.

8. The surgical stapler according to claim 7, wherein during the second phase, the controller is further configured to output a second message indicating inadequate blood flow if the oxygen saturation value is outside the second oxygen saturation range.

9. A surgical stapler comprising:

an annular reload including a staple cartridge having a plurality of staples;

an anvil movable relative to the annular reload and configured to compress tissue therebetween;

a knife disposed within the annular reload configured to cut the tissue;

a spectroscopy assembly disposed within the staple cartridge and including a plurality of light sources and a plurality of photodetectors interspersed among the plurality of light sources; and a handle assembly including:

a motor configured to move the anvil; and a controller coupled to the spectroscopy assembly, the controller configured to:

activate the motor during a first phase of clamping to move the anvil to clamp tissue between the anvil and the staple cartridge;

activate the plurality of light sources to irradiate the tissue contacting the staple cartridge with light;

receive signals from the plurality of photodetectors based on reflected light detected by the plurality of photodetectors;

measure an oxygen saturation value in the tissue based on the signals;

compare the oxygen saturation value to a first oxygen saturation range;

output a first message indicating inadequate blood flow if the oxygen saturation value is outside the first oxygen saturation range; and activate the motor during a second phase of the clamping to move the anvil to further clamp the tissue between the anvil and the staple cartridge if the oxygen saturation value is within the first oxygen saturation range.

10. The surgical stapler according to claim 9, further comprising a display configured to show a graphical user interface, wherein the controller is further configured to output the oxygen saturation value and the first message on the graphical user interface.

11. The surgical stapler according to claim 10, wherein the controller is configured, during the first phase, to move the motor at a first speed.

12. The surgical stapler according to claim 11, wherein the controller is configured, during the second phase, to move the motor at a second speed that is slower than the first speed.

13. The surgical stapler according to claim 12, wherein during the second phase, the controller is further configured to:

measure the oxygen saturation value in the tissue; and compare the oxygen saturation value to a second oxygen saturation range.

14. The surgical stapler according to claim 13, wherein during the second phase, the controller is further configured to:

measure a gap distance between the anvil and the staple cartridge; and compare the measured gap distance to a gap distance range.

15. The surgical stapler according to claim 14, wherein during the second phase, the controller is further configured to enable stapling if the oxygen saturation value is within the second oxygen saturation range and the measured gap distance is within the gap distance range.

16. The surgical stapler according to claim 15, wherein during the second phase, the controller is further configured to output a second message indicating inadequate blood flow if the oxygen saturation value is outside the second oxygen saturation range.

17. A method for real-time tissue perfusion assessment during a clamping procedure using a powered surgical stapler including a motor, a staple cartridge having a plurality of staples, and an anvil movable by the motor relative to the staple cartridge, the method comprising:

activating the motor during a first phase of clamping to move the anvil to clamp tissue between the anvil and the staple cartridge;

measuring an oxygen saturation value in the tissue using a spectroscopy assembly disposed in the staple cartridge;

comparing the oxygen saturation value to a first oxygen saturation range;

outputting a first message indicating inadequate blood flow if the oxygen saturation value is outside the first oxygen saturation range; and activating the motor during a second phase of the clamping to move the anvil to further clamp the tissue between the anvil and the staple cartridge if the oxygen saturation value is within the first oxygen saturation range.

18. The method according to claim 17, further comprising displaying a graphical user interface on a display, the graphical user interface including the oxygen saturation value and the first message.

19. The method according to claim 18, wherein during the first phase, the motor is moved at a first speed and during the second phase, the motor is moved at a second speed that is slower than the first speed.

20. The method according to claim 19, wherein during the second phase, the method further comprises:

measuring the oxygen saturation value in the tissue;

comparing the oxygen saturation value to a second oxygen saturation range;

measuring a gap distance between the anvil and the staple cartridge;

comparing the measured gap distance to a gap distance range;

enabling stapling if the oxygen saturation value is within the second oxygen saturation range and the measured gap distance is within the gap distance range; and outputting a second message on the display indicating inadequate blood flow if the oxygen saturation value is outside the second oxygen saturation range.

* * * * *